United States Patent [19]

Alter et al.

[11] 4,328,382

[45] May 4, 1982

[54] PROCESS FOR SEPARATING OFF OLEFINS FROM GASES CONTAINING OLEFINS

[75] Inventors: Eduard Alter, Dormagen; Ludwig Bruns, Dormagen-Straberg, both of Fed. Rep. of Germany

[73] Assignee: EC Erdolchemie GmbH, Cologne, Fed. Rep. of Germany

[21] Appl. No.: 198,883

[22] Filed: Oct. 20, 1980

[30] Foreign Application Priority Data

Nov. 2, 1979 [DE] Fed. Rep. of Germany ....... 2944151

[51] Int. Cl.³ .............................................. C07C 7/10
[52] U.S. Cl. ..................................... 585/844; 585/843
[58] Field of Search ............................ 585/843, 844

[56] References Cited

U.S. PATENT DOCUMENTS

| 3,960,976 | 6/1976 | Suzuki et al. | 585/843 |
| 4,014,665 | 3/1977 | Steiqelmann | 585/844 |
| 4,132,744 | 1/1979 | Knifton | 585/844 |

OTHER PUBLICATIONS

Crookes et al., J. Chem. Soc. Dalton Transactions, 1973, No. 12, pp. 1241–1247.

*Primary Examiner*—Curtis R. Davis
*Attorney, Agent, or Firm*—Sprung, Felfe, Horn, Lynch & Kramer

[57] ABSTRACT

An improved process for the absorption of an olefin in a silver salt solution and the recovery thereof by desorption is disclosed wherein the silver salt of the silver salt solution is silver trifluoroacetate.

23 Claims, 1 Drawing Figure

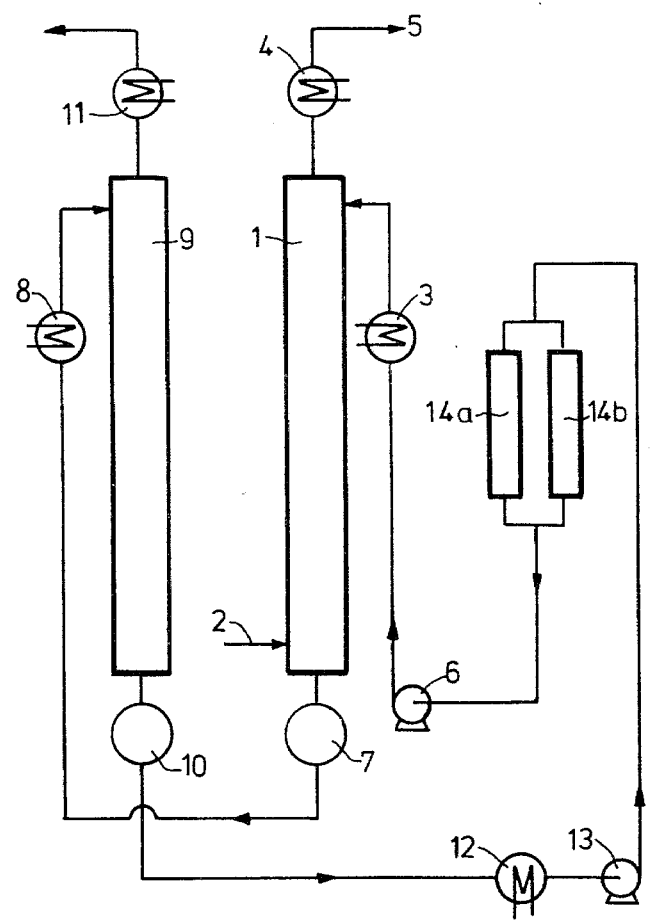

PROCESS FOR SEPARATING OFF OLEFINS FROM GASES CONTAINING OLEFINS

The present invention relates to a process for separating off olefins, from gas streams containing olefins, with the aid of an aqueous silver salt solution, and for recovering the olefins in a pure form from the solution.

In the literature, it has been known for a long time that a number of certain heavy meal ions, for example platinum-II, paladium-II, mercury-II, copper-I and silver-I ions, form complexes with a large number of olefins. The three metal ions last mentioned are of particular industrial interest with regard to the separation of unsaturated hydrocarbons from olefin-containing mixtures.

However, mercury-II salt solutions are excluded from industrial use, since on the one hand the mercury-olefin complex has a very high stability and the olefins can only be liberated by adding alkali or acid at greatly elevated temperature, and on the other hand the high toxicity of mercury makes industrial use seem doubtful.

In the case of the copper-I salts, there is the difficulty of the ease of oxidation of Cu-I to Cu-II, which can lead to considerable difficulties in an industrial plant because of the necessity of exclusion of oxygen.

In contrast, the use of silver tetrafluoborate and silver hexafluosilicate for separating off olefins appears more favourable, since the silver-olefin complexes thereby formed can largely be decomposed again into the metal salt and olefin by boiling up the solution (DE-AS (German Published Specification) No. 1,027,658), and the silver ions are relatively non-toxic. The solubility of the olefins is determined by the silver ion concentration and by the olefin partial pressure. As the silver content and pressure increase, the solubility of the olefins in silver salt solutions increases. However, the silver salt solutions mentioned in the DE-AS (German Published Specification) mentioned have the following disadvantages: silver tetrafluoborate and silver hexafluosilicate are very sensitive towards hydrolysis, which in aqueous solution can only be suppressed with an excess of fluoboric acid or hydrofluoric acid. The acid freely present in the solution imposes considerable demands on the materials for the equipment when the process is carried out industrially. Thus, for example, materials such as gold, platinum or graphite must be employed.

Furthermore, when silver tetrafluoborate is employed, silver salt solutions of substantial concentration may be prepared, which absorb considerable amounts of olefins but do not release the olefins quantitatively during subsequent boiling up, for example at 90° to 100° C. In order to release as much olefins as possible during the desorption, this operation is therefore carried out in vacuo, which means a further technical effort since, for example, the olefin gas desorbed in vacuo must be subjected to a subsequent increase of pressure. Moreover, under these conditions, considerable amounts of free acid pass from the solution into the gas phase in the desorption stage, so that the olefin stream obtained must be subjected to a subsequent alkaline washing to remove acid. This means a loss of acid and an expenditure on chemicals for the neutralization thereof. The washing to remove acid in the process described must furthermore be carried out in a particularly troublesome manner for certain processes, for example for the use of desorbed ethylene in the preparation of ethylene oxide, since uncontrollable amounts of halogen compounds act as catalyst poisons in the preparation of ethylene oxide. In addition, it is recommended that when the absorption of olefins by means of silver tetrafluoborate solution is carried out industrially, an olefin partial pressure of 2 bars should not be exceeded (Erdöl und Kohle, Erdgas, Petrochemie, 16, 551 et seq. (1963). The reason for this is that in the presence of tetrafluoboric acid under pressures of above 2 bars and at temperatures of 10°–40° C., the olefins tend to form oligomers, which make it necessary to change the silver salt solution after a certain operating time.

The disadvantages described have evidently prevented the proposed processes from being applied on an industrial scale.

A process has now been found for separating off olefins from gases containing olefins, by adsorption of the olefins in an aqueous solution of a silver salt and recovery of the olefins in a pure form by desorption from the silver salt solution, which is characterised in that silver trifluoroacetate is used as the silver salt and the absorption of the olefins is carried out, in a manner which is in itself known, under a higher pressure and/or at a lower temperature than the desorption.

The concentration of the aqueous solution of silver trifluoroacetate employed in the process according to the invention can be, for example, 400 to 720 g of $CF_3COOAg/l$, preferably 500 to 600 g/l.

Olefins which may be mentioned for the process according to the invention are, for example, straight-chain or branched monomers for vinyl polymerization which have one or more, preferably one, double bond(s) and 2 to 6, preferably 4 and particularly preferably 2 or 3, carbon atoms. Examples of these monomers are: ethylene, propylene, n-but-1-ene, n-but-2-ene, i-butene, butadiene, the isomeric pentenes, the isomeric hexenes, acrylonitrile, vinyl acetate, acrylic acid, acrylates, methacrylic acid and methacrylates. Ethylene and propylene are preferably separated off, and ethylene is particularly preferably separated off.

The olefin-containing gases can also contain, in addition to one or more of the olefins mentioned, saturated hydrocarbons, carbon dioxide, carbon monoxide, oxygen, hydrogen, nitrogen or noble gases, for example argon. The substances mentioned can be present in the olefin-containing gas in greatly varying amounts without the procedure of the process according to the invention thereby being adversely affected. The amount of olefins in the olefin-containing off-gas likewise does not impair the feasibility of the process according to the invention. A content of about 5 to over 95% by volume of olefins in the olefin-containing gas may be mentioned as an example. Quite generally, the amount of olefin in the olefin-containing gas depends on the preceding process, in which the olefin-containing gas is obtained.

The application of the process according to the invention to the separation of ethylene from an off-gas from the preparation of ethylene oxide may be mentioned as an example. The following composition may be mentioned as typical of such an off-gas in the case where the preparation of ethylene oxide is carried out with methane as the inert gas diluent: 35–55% by volume of methane, 20–35% by volume of ethylene, 4–6% by volume of carbon dioxide, 3–6% by volume of oxygen, 0.1 to 10% by volume of argon and 0.1–10% by volume of nitrogen. In the case where nitrogen is used as the inert gas diluent instead of methane in the preparation of ethylene oxide, the content of methane given can fall to 0, whilst the nitrogen content can assume values of 35–60% by volume.

A temperature range from about 10° to about 60° C., preferably about 15° to about 30° C., may be mentioned as an example of the temperature for the absorption of the olefines. A temperature range from about 15° to about 100° C., preferably about 50° to about 90° C., may be mentioned as an example of the temperature for the desorption.

Normal pressure or increased pressure, for example in the range from 1 to 25 bars, preferably in the range from 1 to 15 bars, may be mentioned as the pressure for the absorption of the olefins. Reduced pressure, normal pressure or slightly increased pressure, for example in the range from 0.05 to 4 bars, preferably 1 to 4 bars, may be mentioned as the pressure for the desorption of the olefins. The desorption of the olefins can particularly preferably be carried out under normal pressure, because of the simplicity of the apparatus.

The absorption and desorption of the olefins in the process according to the invention are carried out under various pressure/temperature conditions. Thus, for example, the absorption of the olefins can be carried out under a higher pressure than the desorption. The absorption of the olefins can, however, also be carried out at a lower temperature than the desorption. Finally, a combination of both measures can be applied. Devices which make the required changes in pressure and/or temperature possible, for example pumps and pressure-release valves and/or cooling and heating devices, are located on or between the absorption and desorption apparatuses in order to effect these measures.

The combination of pressure and temperature differences in the absorption and desorption stage is the preferred procedure of the process according to the invention. In this case, a temperature of about 15° to about 30° C. and an increased pressure is established for the absorption and a temperature of about 50° to about 90° C. and normal pressure is established for the desorption. In a particularly preferred embodiment, an increased pressure of more than 2 bars is established in the absorption stage, whilst the other parameters remain unchanged.

The process according to the invention can be carried out discontinuously or continuously. The continuous procedure is preferred. In this case, an aqueous solution of silver trifluoroacetate is pumped continuously through an absorption apparatus, where it becomes charged with the olefins from the olefin-containing gas, and is then pumped into a desorption apparatus, where the olefins are recovered in a pure form, and thereafter is pumped back into the absorption stage. Possible absorption apparatuses are the apparatuses known to the expert which have suitable built-in fitments enabling the olefin-containing gases and the silver trifluoroacetate solution to be brought into intimate contact. Examples of such built-in fitments are: column packings, built-in trays, sieves or baffles or nozzles for fine distribution of the silver trifluoroacetate solution. Possible desorption apparatuses are those apparatuses which are known to the expert and have built-in fitments enabling the silver trifluoroacetate solution charged with the olefins to be finely distributed in order to achieve a large surface area. Examples of apparatuses which can be used are those which have been described for the absorption. It may be useful to bubble suitable gases in countercurrent through the silver trifluoroacetate solution charged with the olefins in order to assist the desorption of the olefins. Examples of such gases which may be mentioned are nitrogen, methane and steam.

The process according to the invention makes it possible to separate off olefins selectively from an olefin-containing gas. About 85 to 95 % of the olefins present in the olefin-containing gas can be recovered. The olefins recovered have a purity of more than 98% by volume.

It is surprising that, compared with the state of the art, the process according to the invention, in which the silver content of the absorption solution is only about half as high, exhibits the same absorption capacity. It is furthermore surprising that no conversion of the absorbed olefins into oligomers takes place in the process according to the invention, so that the absorption solution remains usable over a virtually unlimited period.

An acid-free absorption solution is employed in the process according to the invention, so that the choice of materials for the equipment is facilitated. Furthermore, no free acid passes into the pure olefins during desorption of the olefins, so that subsequent washing to remove acid from the pure olefins can be dispensed with. Although the desorption can, according to the invention, also be carried out with the application of reduced pressure, it already takes place quantitatively under normal pressure or slightly increased pressure, for example up to about 2 bars, and at a temperature of about 80° to about 90° C., so that it is not necessary to carry out the operation in vacuo, which requires technical effort. In contrast to the statements of the state of the art, the process according to the invention can also be performed under pressures of over 2 bars without adverse phenomena, such as, for example, oligomerization of the absorbed olefins, being observed.

BRIEF DESCRIPTION OF THE DRAWING

Referring to the annexed drawing, the same is a flow diagram showing a mode for carrying out the process of the invention.

EXAMPLES

The following examples are carried out continuously in a circulatory apparatus, as shown in FIG. 1.

The olefin-containing gas enters, at (2), the absorber (1), where the olefin is absorbed by the silver trifluoroacetate solution, which is passed through in countercurrent. The off-gas is passed over the condenser (4), to separate off water, to the outlet (5). The absorption solution charged with olefin passes via a stock vessel (7) and a pre-heater (8) into the desorber (9). The desorbed pure olefin is put to use again via the condenser (11), to separate off water. The absorption solution is introduced via the stock vessel (10) the cooler (12) and the pump (13) into the storage tanks (14a, 14b), from where it is recycled into the absorber (1) via the pump (6) and the cooler (3).

EXAMPLE 1

A silver trifluoroacetate solution containing 600 g of $CF_3COOAg/l$ is used. The amount circulating is 1.2 l/hour. The absorber is charged with 60 l/hour of an ethylene-containing stream of off-gas.

The experimental data are summarized in the two tables which follow.

EXAMPLE 2

A circulatory apparatus in which the absorption can be carried out under pressure is used. Desorption is carried out under an increased pressure of 2 bars. A silver trifluoroacetate solution containing 530 g of CF$_3$COOAg/l is used. The experimental data are summarized below.

| Absorber | 14 bars | T = 20° C. |
|---|---|---|
| Desorber | 3 bars | T = 80° C. |
| Gas fed to the absorber | 800 Nl/hour | |
| Circulating solution | 6 l | |

| | Feed | | Off-gas | | Pure ethylene | |
|---|---|---|---|---|---|---|
| | Nl/hour | % by volume | Nl/hour | % by volume | Nl/hour | % by volume |
| CH$_4$ | 410.4 | 51.3 | 409.1 | 70.9 | 1.3 | 0.6 |
| C$_2$H$_4$ | 242.4 | 30.3 | 21.6 | 3.7 | 220.8 | 99.0 |
| CO$_2$ | 33.6 | 4.2 | 32.9 | 5.7 | 0.7 | 0.3 |
| O$_2$ | 38.4 | 4.8 | 38.2 | 6.7 | 0.2 | 0.1 |
| Ar | 64.0 | 8.0 | 64.0 | 11.1 | — | <0.1 |
| N$_2$ | 11.2 | 1.4 | 11.2 | 1.9 | — | <0.1 |
| | 800 | | 577 | | 223 | |

About 91% of the ethylene contained in the feed gas are recovered.

EXAMPLE 3

A circulatory apparatus in which the absorption is carried out under slightly increased pressure is used. The desorption is carried out under atmospheric pressure. The absorber is charged with a propylene-containing stream of gas. The silver trifluoroacetate solution used contains 600 g of CF$_3$COOAg/l. The experimental data are summarized below.

| Absorber | 1.25 bars | T = 20° C. |
|---|---|---|
| Desorber | 1 bar | T = 80° C. |
| Gas fed to the absorber | 60 Nl/hour | |
| Circulating solution | 1.2 l/hour | |

| | Feed | | Off-gas | | Pure propylene | |
|---|---|---|---|---|---|---|
| | Nl/hour | % by volume | Nl/hour | % by volume | Nl/hour | % by volume |
| N$_2$ | 34.1 | 56.8 | 33.7 | 94.9 | 0.4 | 1.6 |
| C$_3$H$_6$ | 24.6 | 41.1 | 0.5 | 1.4 | 24.1 | 98.4 |
| C$_3$H$_8$ | 1.3 | 2.1 | 1.3 | 3.7 | — | 0.01 |
| | 60.0 | | 35.5 | | 24.5 | |

About 98% of the propylene contained in the feed are recovered.

| Absorber | p = 1.27 bars; | T = 20° C. |
|---|---|---|
| Desorber | p = 1.0 bar; | T = 90° C. |
| Gas fed to the absorber | 60 Nl/hour | |
| Circulating solution | 1.2 l/hour | |

| | Feed | | Off-gas | | Pure ethylene | |
|---|---|---|---|---|---|---|
| | Nl/hour | % by volume | Nl/hour | % by volume | Nl/hour | % by volume |
| CH$_4$ | 32.0 | 53.4 | 32.0 | 77.2 | * | 0.1 |
| C$_2$H$_4$ | 19.2 | 32.0 | 0.8 | 1.9 | 18.4 | 99.0 |
| CO$_2$ | 2.9 | 4.8 | 2.8 | 6.7 | * | 0.26 |
| O$_2$ | 2.9 | 4.8 | 2.9 | 7.0 | * | 0.02 |
| Ar | 2.2 | 3.7 | 2.2 | 5.3 | * | 0.01 |
| N$_2$ | 0.8 | 1.3 | 0.8 | 1.9 | * | 0.01 |
| | 60.0 | | 41.5 | | 18.5* | |

*Difference (18.5–18.4 Nl/hour) is the sum of CH$_4$, CO$_2$, O$_2$, Ar and N$_2$.

About 95% of the ethylene contained in the feed gas are recovered.

What is claimed is:

1. In a process for separating an olefin from a gaseous composition containing the same wherein the olefin is absorbed in an aqueous solution of a silver salt and the solution is thereafter desorbed to release olefin from the solution, the improvement wherein said silver salt is silver trifluoroacetate.

2. A process according to claim 1, wherein the absorption of the olefin in the silver salt solution is effected at a pressure at 1 to 25 bars.

3. A process according to claim 2, wherein the desorption of the olefin from the silver solution is effected at a pressure of 0.05 to 4 bars.

4. A process according to claim 2, wherein the silver trifluoroacetate is present in the aqueous absorption solution in the concentration of 400 to 720 grams of silver trifluoroacetate per liter of solution.

5. A process according to claim 1, wherein the absorption of olefin is carried out under a pressure of more than 2 bars.

6. A process according to claim 2, wherein the silver trifluoroacetate is present in the aqueous absorption solution in the concentration of 500 to 660 grams of silver trifluoroacetate per liter of solution.

7. A process according to claim 1, wherein said olefin is ethylene.

8. A process according to claim 7, wherein said ethylene is in admixture with methane.

9. A process according to claim 7, wherein said ethylene is in admixture with carbon dioxide.

10. A process according to claim 7, wherein said ethylene is in admixture with oxygen.

11. A process according to claim 7, wherein said ethylene is in admixture with argon.

12. A process according to claim 7, wherein said ethylene is in admixture with nitrogen.

13. A process according to claim 1, wherein said olefin is propylene.

14. A process according to claim 13, wherein said propylene is in admixture with propane.

15. A process according to claim 13, wherein said propylene is in admixture with nitrogen.

16. A process according to claim 1, wherein said olefin is in admixture with a saturated hydrocarbon.

17. A process according to claim 1, wherein said olefin is in admixture with carbon dioxide.

18. A process according to claim 1, wherein said olefin is in admixture with carbon monoxide.

19. A process according to claim 1, wherein said olefin is in admixture with oxygen.

20. A process according to claim 1, wherein said olefin is in admixture with hydrogen.

21. A process according to claim 1, wherein said olefin is in admixture with nitrogen.

22. A process according to claim 1, wherein said olefin is in admixture with a noble gas.

23. A process according to claim 1, wherein said olefin is ethylene and the gaseous composition containing said olefin is an off-gas from the preparation of ethylene oxide.

* * * * *

UNITED STATES PATENT AND TRADEMARK OFFICE
CERTIFICATE OF CORRECTION

PATENT NO. : 4,328,382
DATED : May 4, 1982
INVENTOR(S) : Eduard Alter, Ludwig Bruns It is certified that error appears in the above-identified patent and that said Letters Patent are hereby corrected as shown below:

| Column | line | |
|---|---|---|
| 2 | 16 | delete "adsorption" and insert --absorption--. |
| 2 | 28 | delete "600" and insert --660--. |

Signed and Sealed this

Third Day of August 1982

[SEAL]

Attest:

Attesting Officer

GERALD J. MOSSINGHOFF
Commissioner of Patents and Trademarks